United States Patent
Liang et al.

(10) Patent No.: US 10,729,675 B2
(45) Date of Patent: Aug. 4, 2020

(54) GOSSYPOL ISATIN SCHIFF BASE COMPOUNDS WITH ANTITUMOR ACTIVITIES AND A METHOD OF PREPARING THE SAME

(71) Applicants: Chengyuan Liang, Xi'an (CN); Xingke Ju, Xi'an (CN); Shunjun Ding, Xi'an (CN); Lei Tian, Xi'an (CN); Yuzhi Liu, Xi'an (CN); Xiaolin Xie, Xi'an (CN); Dezhu Zhang, Xi'an (CN); Wenbo Yao, Xi'an (CN); Dan Yang, Xi'an (CN)

(72) Inventors: Chengyuan Liang, Xi'an (CN); Xingke Ju, Xi'an (CN); Shunjun Ding, Xi'an (CN); Lei Tian, Xi'an (CN); Yuzhi Liu, Xi'an (CN); Xiaolin Xie, Xi'an (CN); Dezhu Zhang, Xi'an (CN); Wenbo Yao, Xi'an (CN); Dan Yang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 56 days.

(21) Appl. No.: 16/270,567

(22) Filed: Feb. 7, 2019

(65) Prior Publication Data
US 2020/0147042 A1    May 14, 2020

(30) Foreign Application Priority Data
Nov. 13, 2018 (CN) .......................... 2018 1 1341648

(51) Int. Cl.
*A61K 31/404* (2006.01)
*A61P 35/00* (2006.01)
*G01N 33/50* (2006.01)

(52) U.S. Cl.
CPC ............ *A61K 31/404* (2013.01); *A61P 35/00* (2018.01); *G01N 33/5011* (2013.01)

(58) Field of Classification Search
None
See application file for complete search history.

(56) References Cited

U.S. PATENT DOCUMENTS

2009/0010878 A1* 1/2009 Holmlund .............. A61K 31/11
424/85.2

* cited by examiner

*Primary Examiner* — Kamal A Saeed

(57) ABSTRACT

A gossypol isatin Schiff base compound with antitumor activities represented by formula I:

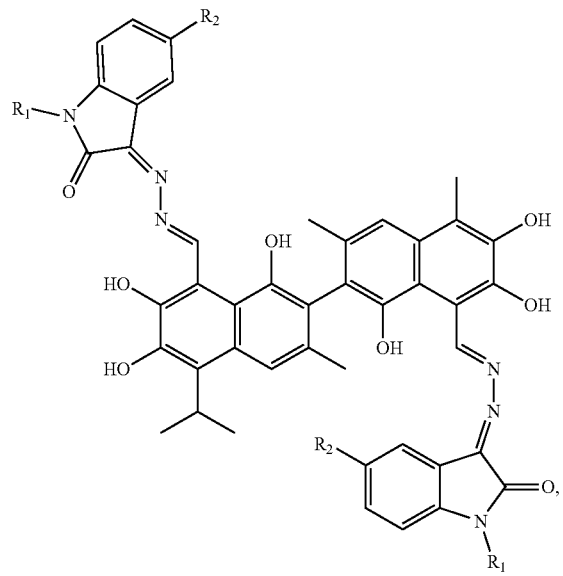

$R_1$ and $R_2$ are independently hydrogen, alkyl, cycloalkyl, alkoxy, nitro, halogen, unsubstituted or substituted phenyl, or unsubstituted or substituted benzyl. A method of preparing the compound of formula I is also disclosed.

15 Claims, No Drawings

GOSSYPOL ISATIN SCHIFF BASE COMPOUNDS WITH ANTITUMOR ACTIVITIES AND A METHOD OF PREPARING THE SAME

The present invention claims priority to Chinese Patent Application No. 201811341648.X, Filed on Nov. 13, 2018, which is incorporated by reference for all purposes as if fully set forth herein.

BACKGROUND OF THE INVENTION

Field of the Invention

The present invention relates to the field of pharmaceutical chemistry, and more particularly, to gossypol isatin Schiff base compounds with antitumor activities and a method of preparing the same.

Discussion of the Related Art

Gossypol is a polyphenolic bis-naphthalene aldehyde compound, and a natural yellow pigment found in small cell glands between cotton cells. It is an inhibitor of the anti-apoptotic protein of the Bcl-2 family, not only effectively blocking the binding pocket of Bcl-2, Bcl.-xL and BH3, but also blockers binding to Mcl-1 (a homologous protein of Bcl-2).

Isatin and its derivatives have unique electronic properties and biological activities. They can be synthesized in large industrial scale, and are relatively inexpensive raw materials. Many chemical reactions can be occurred at the 1, 2, and 3 positions and benzene ring of isatin, and its derivatives can be synthesized via different reactions.

Schiff bases have unique structural characteristics, i.e., N atom in the core structure has a lone pair of electrons. The lone pair of electrons makes Schiff bases common ligands in coordination chemistry. Schiff bases can have two different groups that can react with various groups to obtain different derivatives, and can be used widely in chemical and biological applications.

The inventors designed and synthesized gossypol isatin Schiff base compounds with gossypol and isatin and its derivatives as starting materials.

SUMMARY OF THE INVENTION

In one embodiment, the present invention provides a gossypol isatin Schiff base compound with antitumor activities represented by formula I:

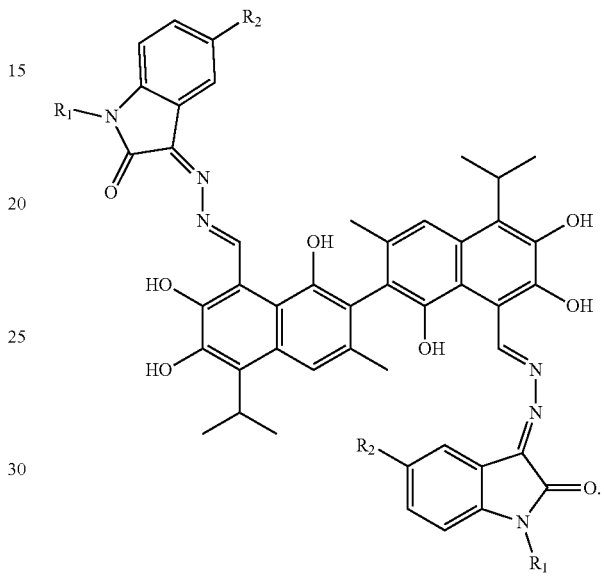

I

In formula I, $R_1$ and $R_2$ are independently hydrogen, alkyl, cycloalkyl, alkoxy, nitro, halogen, unsubstituted or substituted phenyl, or unsubstituted or substituted benzyl.

In another embodiment, $R_1$ is independently hydrogen, alkyl, or benzyl.

In another embodiment, $R_2$ is independently hydrogen, alkyl, or halogen.

In another embodiment, the compound is selected from the group consisting of:

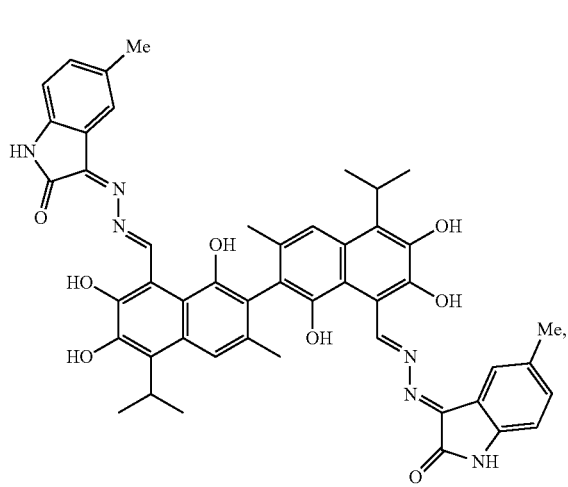

(1)

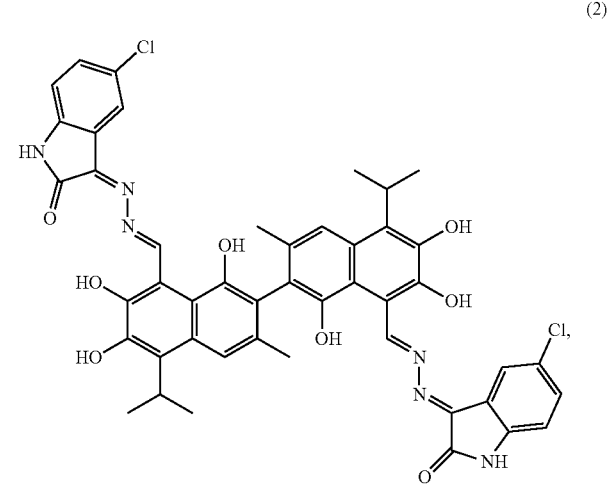

(2)

-continued
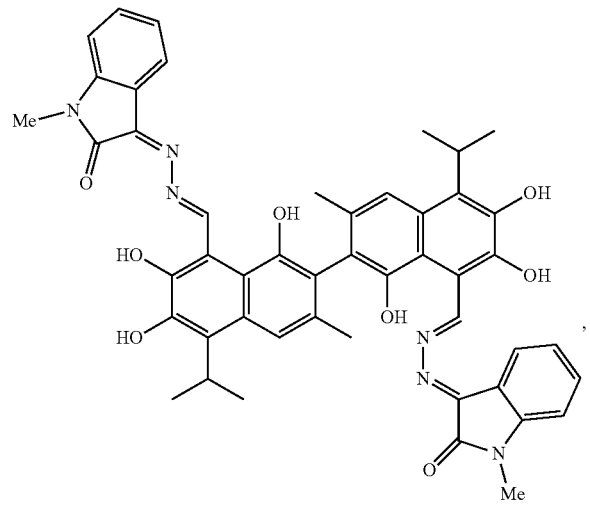
(3)
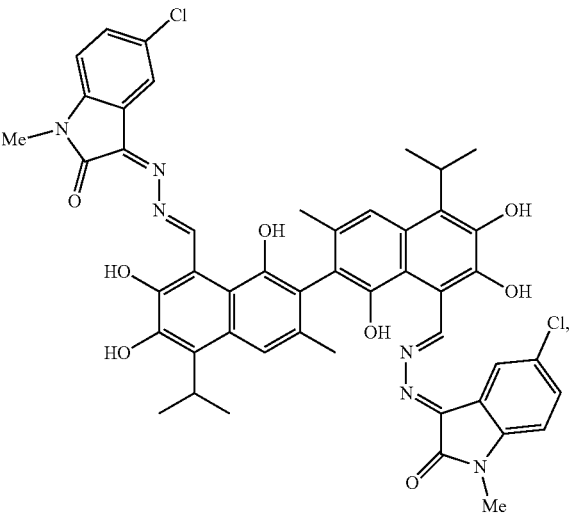
(4)
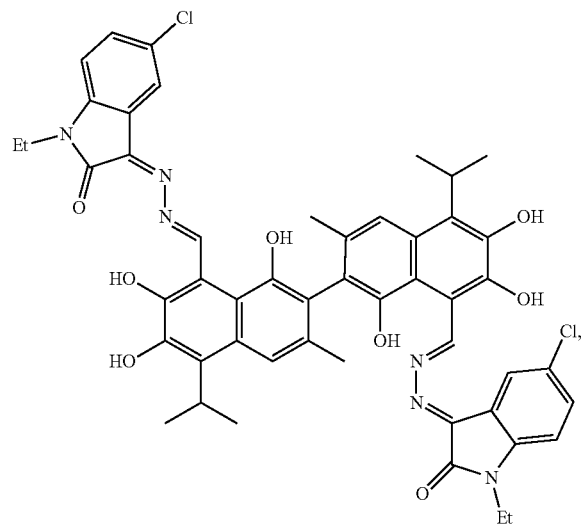
(5)
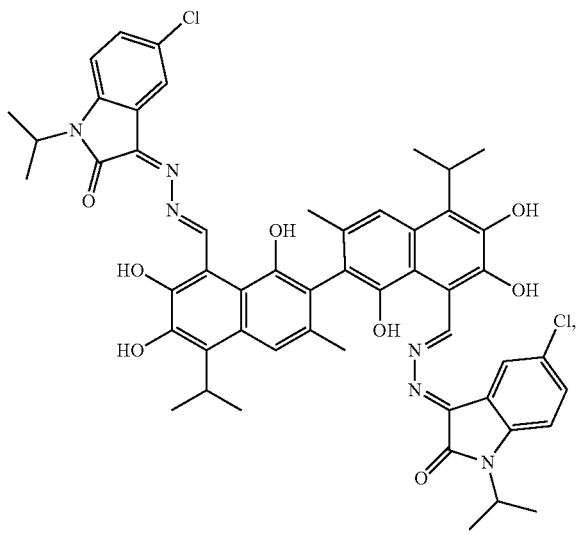
(6)

(7)
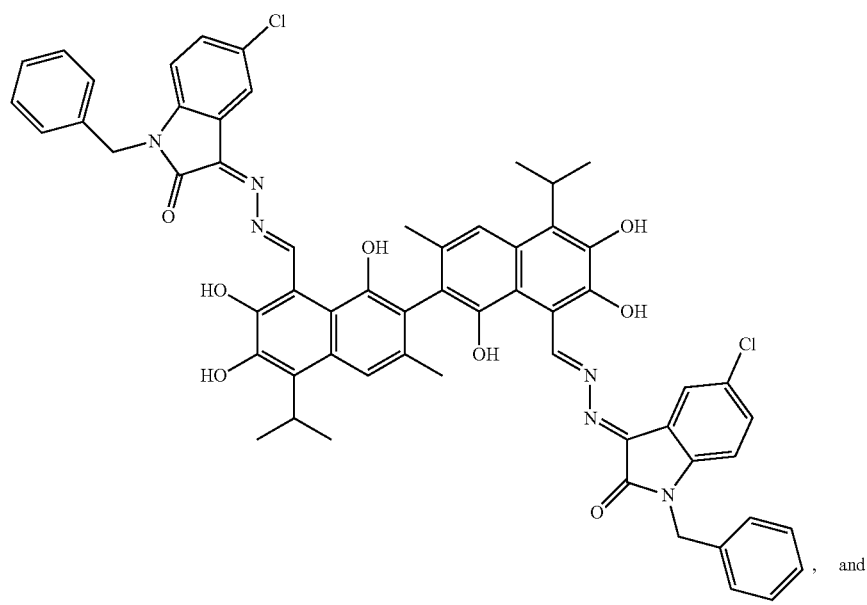
, and
(8)
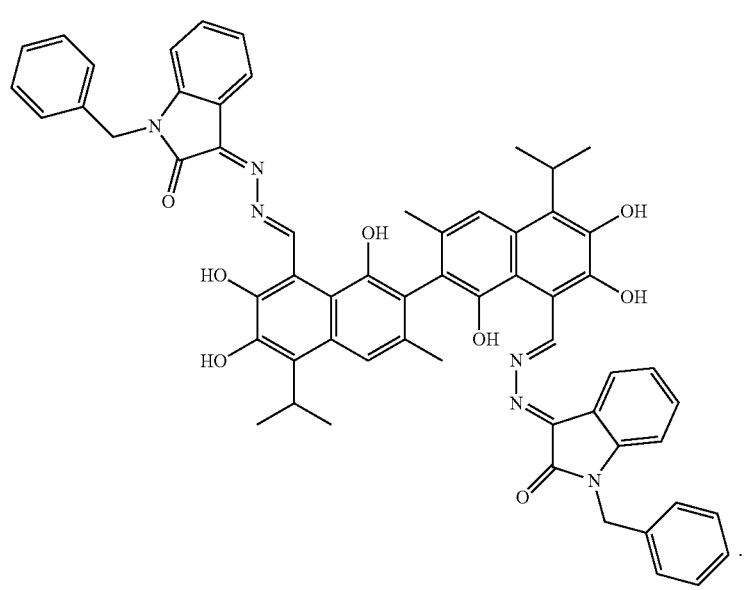
.
In one embodiment, the present invention provides a method of preparing the compound of formula I. The method includes:
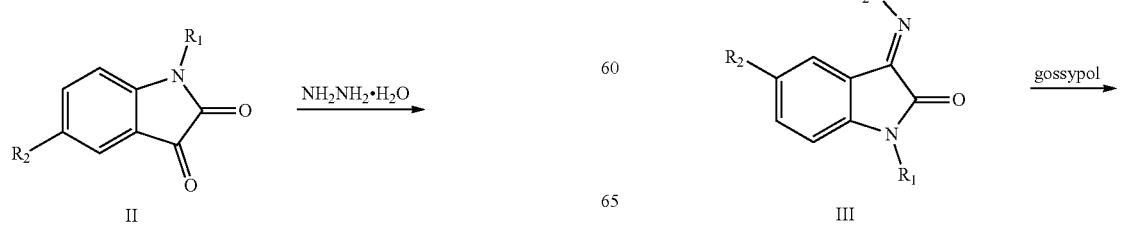

-continued

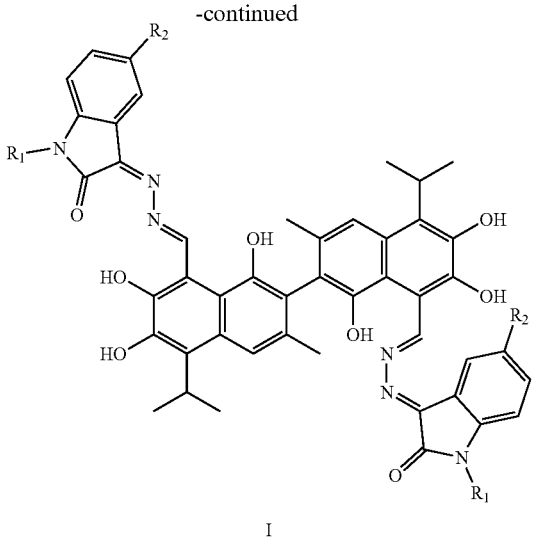

I (1) reacting a compound of formula II and hydrazine hydrate ($N_2H_4 \cdot H_2O$) in an organic solvent to obtain a compound of formula III; and (2) reacting the compound of formula III with gossypol in the presence of a catalyst in the organic solvent to obtain the compound of formula I. $R_1$ and $R_2$ are independently hydrogen, alkyl, cycloalkyl, alkoxy, nitro, halogen, unsubstituted or substituted phenyl, or unsubstituted or substituted benzyl.

In another embodiment, the organic solvent is methanol, ethanol, or isopropanol.

In another embodiment, the organic solvent is ethanol.

In another embodiment, the compound of formula II and hydrazine hydrate ($N_2H_4 \cdot H_2O$) are heated in the organic solvent to 60-100° C. for 4 to 10 hours.

In another embodiment, the compound of formula III and gossypol are heated in the organic solvent to 60-100° C. for 8 to 14 hours.

In another embodiment, the method further includes recrystallizing the compound of formula I in the organic solvent.

In another embodiment, a molar ratio of the compound of formula II and hydrazine hydrate ($N_2H_4 \cdot H_2O$) is 1:1 to 1:2.5.

In another embodiment, the molar ratio of the compound of formula II and hydrazine hydrate ($N_2H_4 \cdot H_2O$) is 1:1.5.

In another embodiment, a molar ratio of the compound of formula III and gossypol is 2:1 to 3:1.

In another embodiment, the molar ratio of the compound of formula III and gossypol is 2.5:1.

In another embodiment, the catalyst is piperidine or triethylamine.

In one embodiment, the present invention provides a method of using the compound of formula I in antitumor drug research, development, and application.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention.

As used herein, the term alkyl refers to a monovalent straight or branched chain, saturated aliphatic hydrocarbon radical having 1-8 carbon atoms. For example, alkyl refers to any of the hexyl alkyl and pentyl alkyl isomers as well as n-, iso-, sec- and t-butyl, n- and iso-propyl, ethyl, or methyl. The term cycloalkyl refers to any monocyclic ring of an alkane having 1-8 carbon atoms. For example, cycloalkyl refers to cyclopropyl, cyclobutyl, cyclopentyl, or cyclohexyl. The alkoxy refers to an alkyl ether group wherein the alkyl moiety is as defined above.

Alkyl, cycloalkyl, and alkoxy also include saturated aliphatic hydrocarbon radicals wherein one or more hydrogens are replaced with deuterium, for example, $CD_3$.

The term halogen refers to fluorine, chlorine, bromine or iodine.

The term substituted phenyl refers to a phenyl substituted with 1-3 halogen, hydroxyl, nitro, alkyl, or alkoxy groups. The term substituted benzyl refers to a benzyl substituted with 1-3 halogen, hydroxyl, nitro, alkyl, or alkoxy groups.

The present invention provides gossypol isatin Schiff base compounds with antitumor activities.

The structures of the gossypol isatin Schiff base compounds (hereafter, compounds) of the present invention are represented formula I:

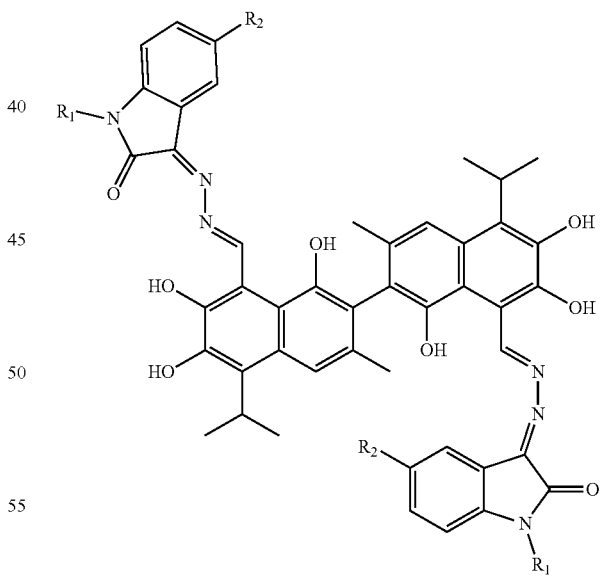

I

In formula I, $R_1$ and $R_2$ are independently hydrogen, alkyl, cycloalkyl, alkoxy, nitro, halogen, unsubstituted or substituted phenyl, or unsubstituted or substituted benzyl.

Preferably, the compounds have the following formulas.

(1)
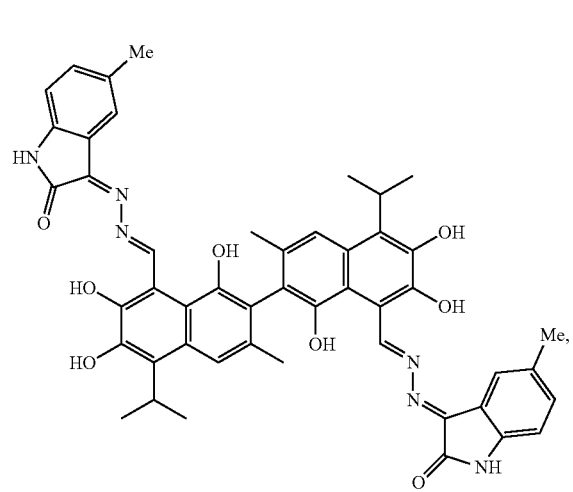
(2)
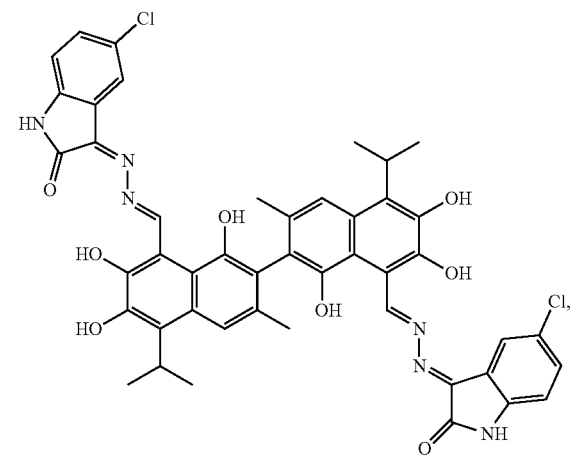
(3)
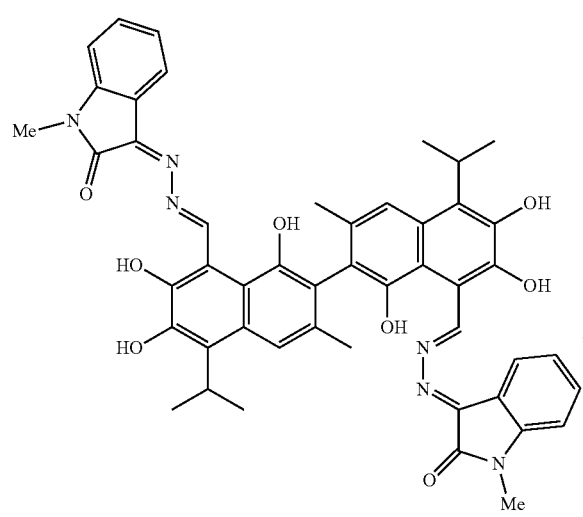
(4)
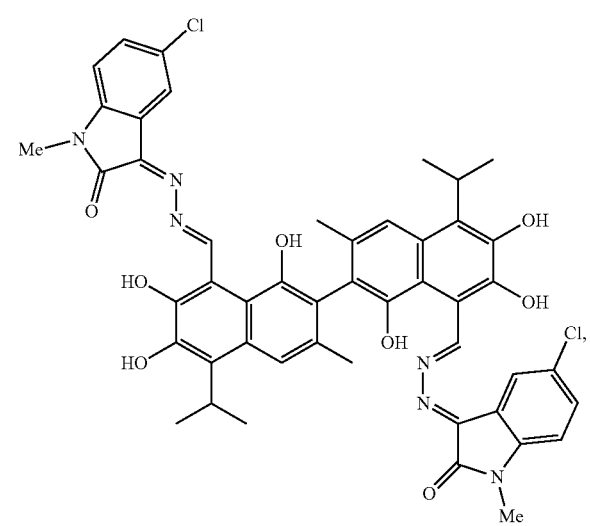
(5)
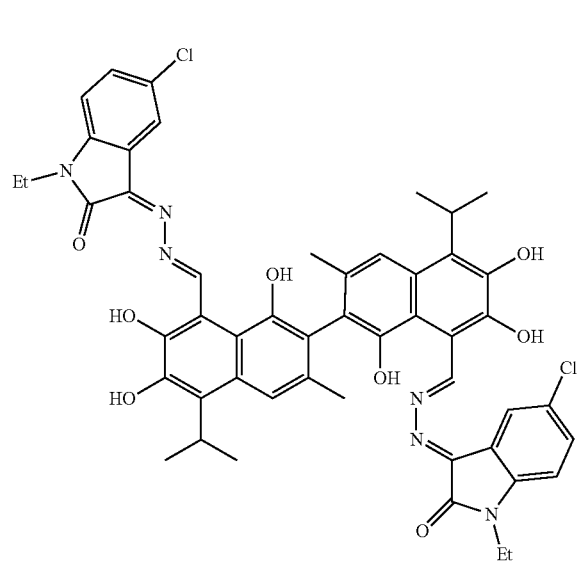
(6)
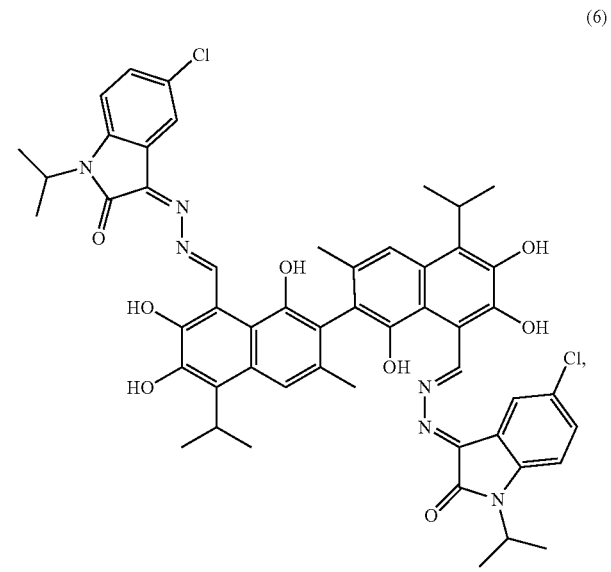

(7)
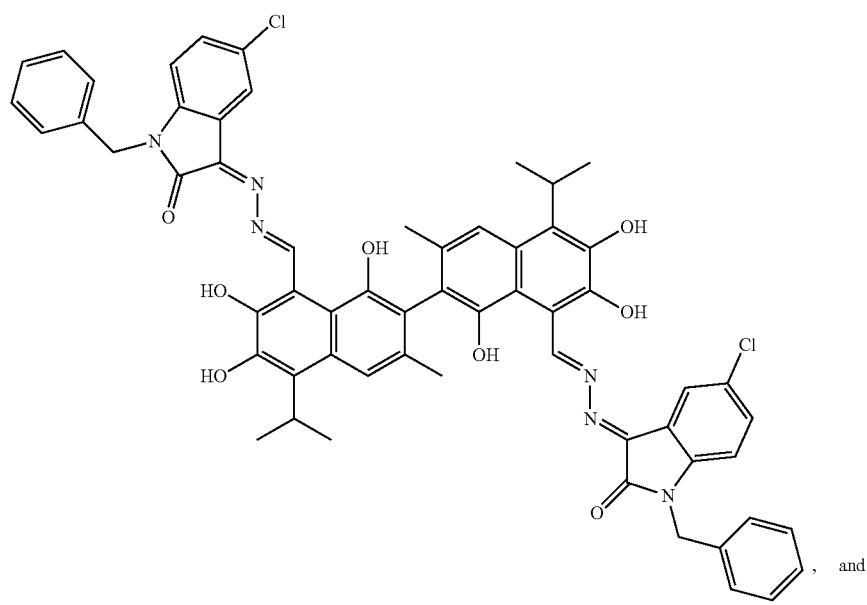
, and
(8)
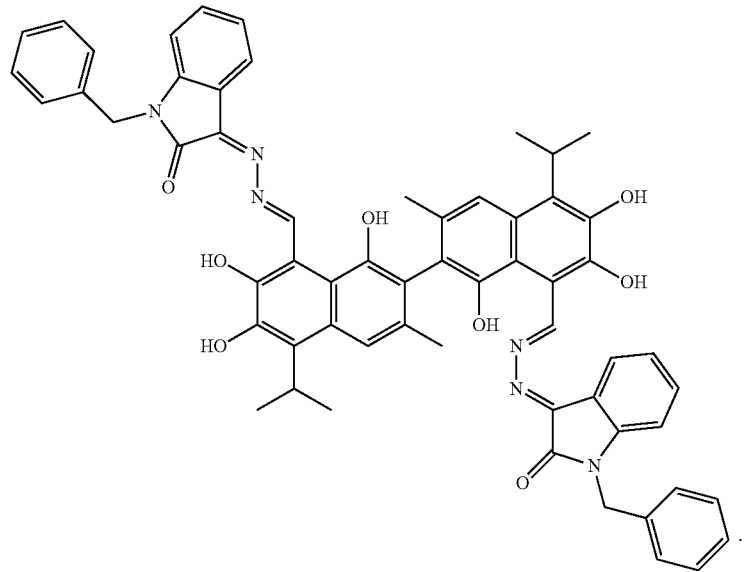
.

The present invention also provides a method of preparing the above-described compounds.

The above-described compounds are obtained by reacting isatin and its derivatives (compounds of formula II) with hydrazine hydride in an organic solvent (e.g., ethanol) under heating and refluxing to form an intermediate (compound of formula III). The intermediate then reacts with gossypol to form a gossypol isatin Schiff base compound (formula I).

Gossypol has the following structure:

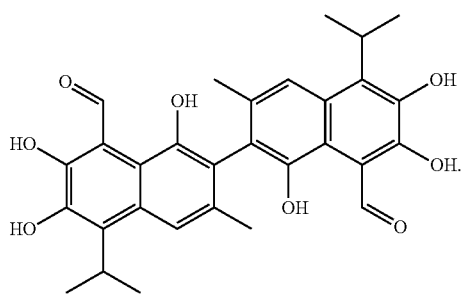 [SMILES: Cc1cc2c(C(C)C)c(O)c(O)c(C=O)c2c(O)c1-c1c(C)cc2c(C(C)C)c(O)c(O)c(C=O)c2c1O]

The synthetic route is as follows:

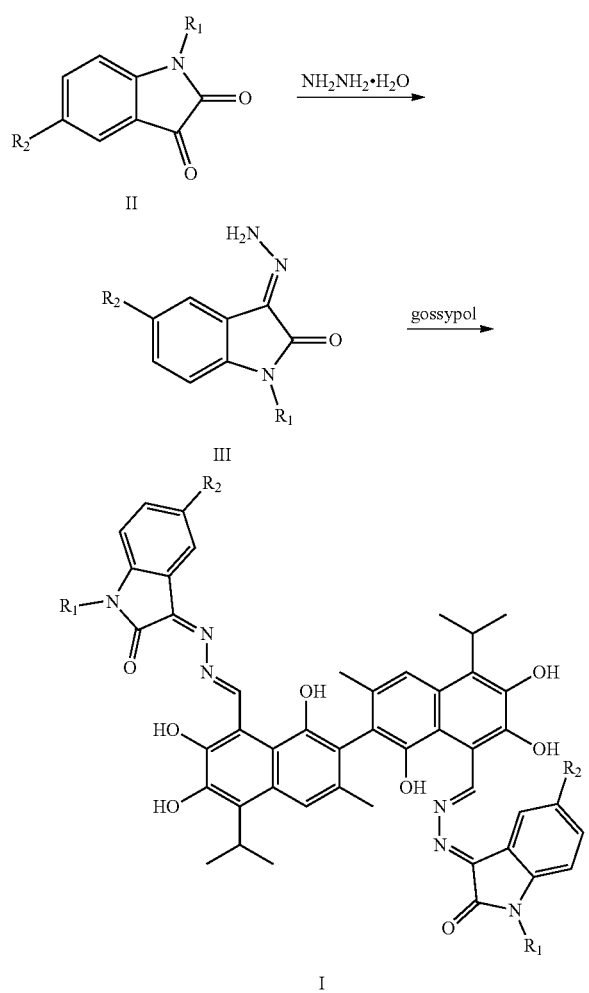

The synthesis route includes the following steps.

(1) reacting isatin or its derivative (a compound of formula II) and hydrazine hydrate ($N_2H_4 \cdot H_2O$) to obtain a compound of formula III; and (2) reacting the compound of formula III with gossypol in the presence of a catalyst in the organic solvent to obtain the compound of formula I.

The organic solvent is methanol, ethanol, or isopropanol, preferably, ethanol.

in a molar ratio of 1:1 to 1:3; and (2) reacting the compound of formula III with gossypol in the presence of a catalyst in the organic solvent to obtain the compound of formula I.

The compound of formula II and hydrazine hydrate ($N_2H_4 \cdot H_2O$) are heated in the organic solvent to 60-85° C. for 5 to 7 hours, and the compound of formula III and gossypol are heated in the organic solvent to 65-85° C. for 8 to 12 hours.

The method may further include: recrystallizing the compound of formula I in the organic solvent.

A molar ratio of the compound of formula II and hydrazine hydrate ($N_2H_4 \cdot H_2O$) is 1:1 to 1:3, preferably, 1:1.5.

A molar ratio of the compound of formula III and gossypol is 2:1 to 3:1, preferably, 2.2:1.

The catalyst is piperidine or triethylamine.

The advantages of the synthetic route are: inexpensive starting materials and environmental friendly, low production costs, mild reaction conditions and safe operation, suitable for industrial production.

INVENTIVE EXAMPLES

The invention will now be further elucidated with reference to specific embodiments. These examples are for illustrative purposes only and are not intended to limit the scope and spirit of the invention.

Example 1: Preparation of Compound (1), (3Z,3'E)-3,3'-(((1E,1'E)-(1,1',6,6',7,7'-hexahydroxy-5,5'-diisopropyl-3,3'-dimethyl-[2,2'-binaphthalene]-8,8'-diyl)bis(methanylylidene))bis(hydrazine-2,1-diylidene))bis(5-methylindolin-2-one)

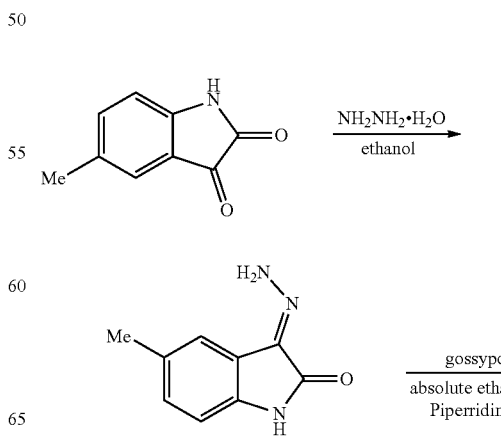

-continued

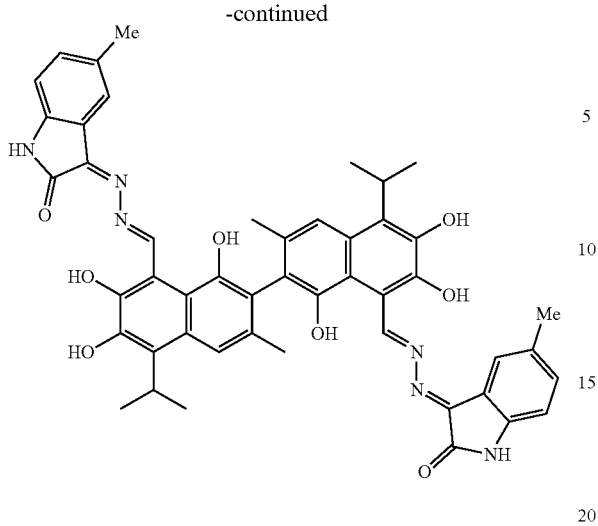

1.61 g (10 mmol) of 5-methylindolin-2,3-dione and 0.75 g (15 mmol) of hydrazine hydride were placed in a three-necked flask and dissolved in 100 mL ethanol. The solution was heated and stirred at 75° C. for 6 hours. After the reaction was complete, the reaction mixture was filtered when it was hot and washed with ethanol. The filtrate was cooled and filtered to obtain an intermediate compound. The intermediate compound and 2.07 g (4 mmol) of gossypol were placed in a reactor, and 0.068 g piperidine and 50 mL of anhydrous ethanol were added. The mixture was then heated and stirred at 75° C. for 10 hours. When thin layer chromatograph (TLC) indicated that the reaction is complete, the reaction mixture was concentrated under reduced pressure. The mixture was cooled to room temperature, filtered, and washed with warm water to give a crude product. The crude product was recrystallized in 25 mL ethanol to give 1.42 g of compound (1) as a yellow crystalline powder, a yield of 42.56%.

(1)

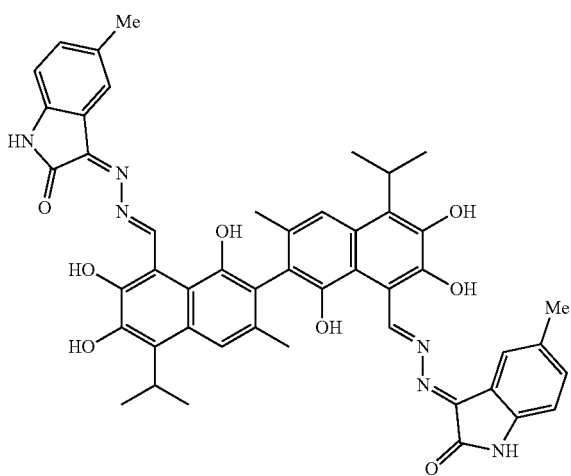

Yellow crystalline powder, M.P. 187.5° C. $^1$H-NMR (400 MHz, DMSO-$d_6$) δ (ppm): 8.94 (1H, s), 8.82 (1H, s), 8.61 (2H, s), 8.47 (2H, s), 7.93 (2H, s), 7.65 (2H, s), 6.70 (2H, d), 5.59 (6H, s), 3.53 (2H, m), 3.18 (6H, s), 2.77 (6H, s), 1.87 (12H, d); $^{13}$C-NMR (100 MHz, DMSO-$d_6$) δ (ppm): 170.6, 155.0, 149.7, 147.2, 145.3, 138.5, 138.2, 135.8, 133.6, 131.7, 129.8, 129.4, 122.4, 119.0, 118.1, 112.5, 102.3, 28.4, 24.8, 21.0; MS (ESI) for (M+H)$^+$: 833.3.

Example 2: Preparation of Compound (2), (3Z,3'E)-3,3'-(((1E,1'E)-(1,1',6,6',7,7'-hexahydroxy-5,5'-diisopropyl-3,3'-dimethyl-[2,2'-binaphthalene]-8,8'-diyl)bis(methanylylidene))bis(hydrazine-2,1-diylidene))bis(5-chloroindolin-2-one)

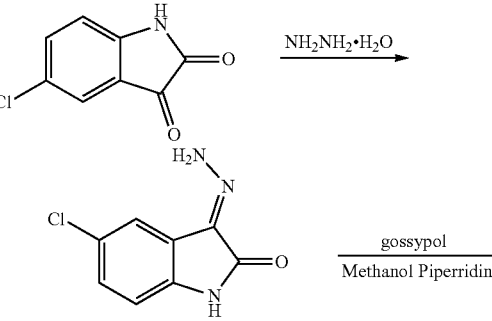

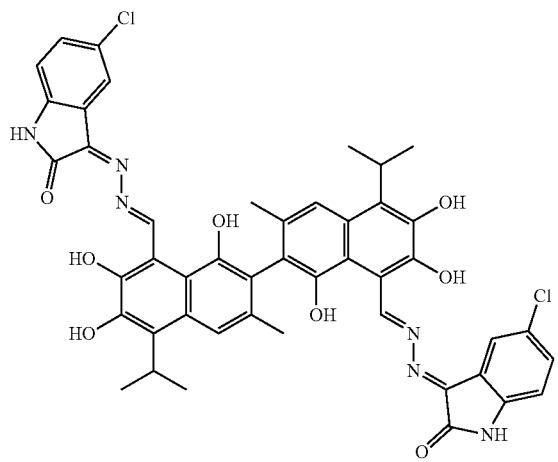

1.81 g (10 mmol) of 5-chloroindolin-2,3-dione and 0.5 g (10 mmol) of hydrazine hydride were placed in a three-necked flask and dissolved in 100 mL methanol. The solution was heated and stirred at 60° C. for 6 hours. After the reaction was complete, the reaction mixture was filtered when it was hot and washed with methanol. The filtrate was cooled and filtered to obtain an intermediate compound. The intermediate compound and 2.07 g (4 mmol) of gossypol were placed in a reactor, and 0.068 g piperidine and 50 mL of methanol were added. The mixture was then heated and stirred at 60° C. for 10 hours. When thin layer chromatograph (TLC) indicated that the reaction is complete, the reaction mixture was concentrated under reduced pressure. The mixture was cooled to room temperature, filtered, and washed with warm water to give a crude product. The crude product was recrystallized in 25 mL methanol to give 1.22 g of compound (2) as a brown yellow crystalline powder, a yield of 34.89%.

(2)

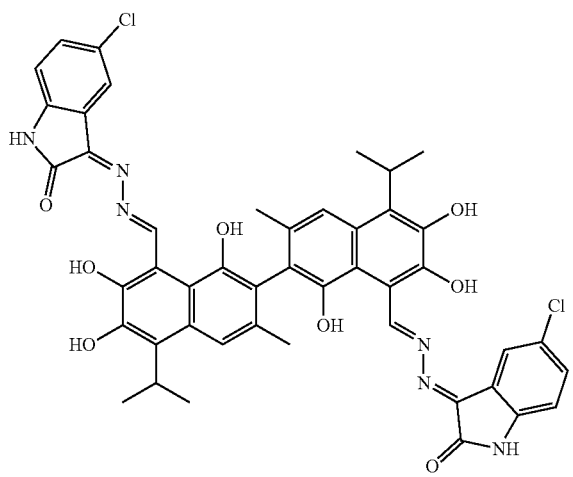

Brown yellow crystalline powder, M.P. 190.7° C. $^1$H-NMR (400 MHz, DMSO-d$_6$) δ (ppm): 8.01 (1H, s), 7.84 (1H, s), 7.69 (2H, s), 7.14 (2H, s), 7.08 (2H, d), 6.97 (2H, s), 6.84 (2H, d), 5.23 (6H, s), 2.41 (2H, m), 2.19 (6H, s), 1.15 (12H, d); $^{13}$C-NMR (100 MHz, DMSO-d$_6$) δ (ppm): 168.4, 151.8, 148.7, 145.9, 143.0, 138.1, 136.5, 131.4, 130.7, 128.6, 127.8, 129.4, 122.4, 119.0, 118.1, 112.5, 102.3, 28.4, 24.8, 21.0; MS (ESI) for (M+H)$^+$: 873.2.

Example 3: Preparation of Compound (3), (3Z,3'E)-3,3'-(((1E, 1'E)-(1,1',6,6',7,7'-hexahydroxy-5,5'-diisopropyl-3,3'-dimethyl-[2,2'-binaphthalene]-8,8'-diyl)bis(methanylylidene))bis(hydrazine-2,1-diylidene))bis(1-methylindolin-2-one)

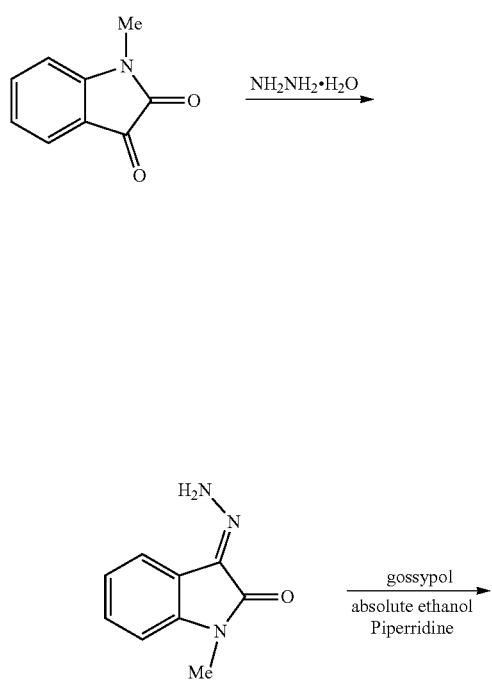

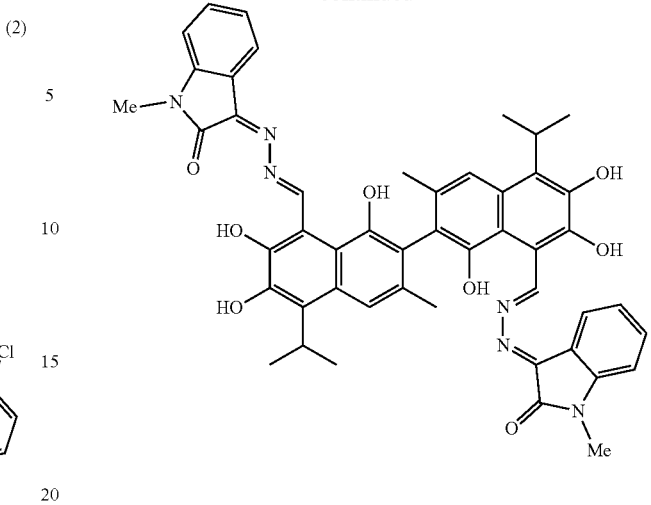

1.61 g (10 mmol) of 1-methylindolin-2,3-dione and 1.25 g (25 mmol) of hydrazine hydride were placed in a three-necked flask and dissolved in 100 mL ethanol. The solution was heated and stirred at 75° C. for 4 hours. After the reaction was complete, the reaction mixture was filtered when it was hot and washed with ethanol. The filtrate was cooled and filtered to obtain an intermediate compound. The intermediate compound and 2.07 g (4 mmol) of gossypol were placed in a reactor, and 0.068 g piperidine and 50 mL of anhydrous ethanol were added. The mixture was then heated and stirred at 75° C. for 14 hours. When thin layer chromatograph (TLC) indicated that the reaction is complete, the reaction mixture was concentrated under reduced pressure. The mixture was cooled to room temperature, filtered, and washed with warm water to give a crude product. The crude product was recrystallized in 25 mL ethanol to give 1.34 g of compound (3) as a yellow crystalline powder, a yield of 40.21%.

(3)

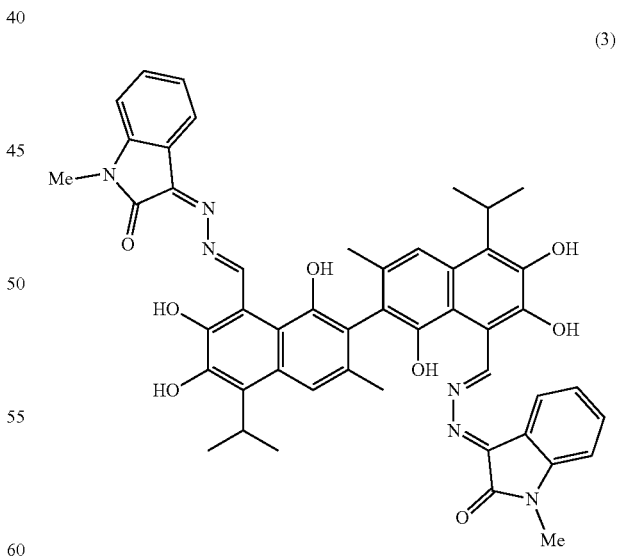

Yellow crystalline powder, M.P. 184.3° C. $^1$H-NMR (400 MHz, DMSO-d$_6$) δ (ppm): 8.46 (1H, s), 8.37 (1H, s), 7.82 (4H, m), 7.49 (2H, s), 7.41 (2H, t), 7.20 (2H, t), 5.22 (6H, s), 3.40 (6H, s), 2.84 (2H, m), 2.68 (6H, s), 1.29 (12H, d); $^{13}$C-NMR (100 MHz, DMSO-d$_6$) δ (ppm): 163.0, 153.7, 150.4, 142.1, 140.6, 138.5, 137.5, 131.7, 130.9, 128.3, 127.0, 122.2, 118.4, 117.7, 114.1, 111.5, 100.4, 30.0, 26.8, 23.4; MS (ESI) for (M+H)$^+$: 833.3.

Example 4: Preparation of Compound (4), (3Z,3'E)-3,3'-(((1E, 1'E)-(1,1',6,6',7,7'-hexahydroxy-5,5'-diisopropyl-3,3'-dimethyl-[2,2'-binaphthalene]-8,8'-diyl)bis(methanylylidene))bis(hydrazine-2,1-diylidene))bis(5-chloro-1-methylindolin-2-one)

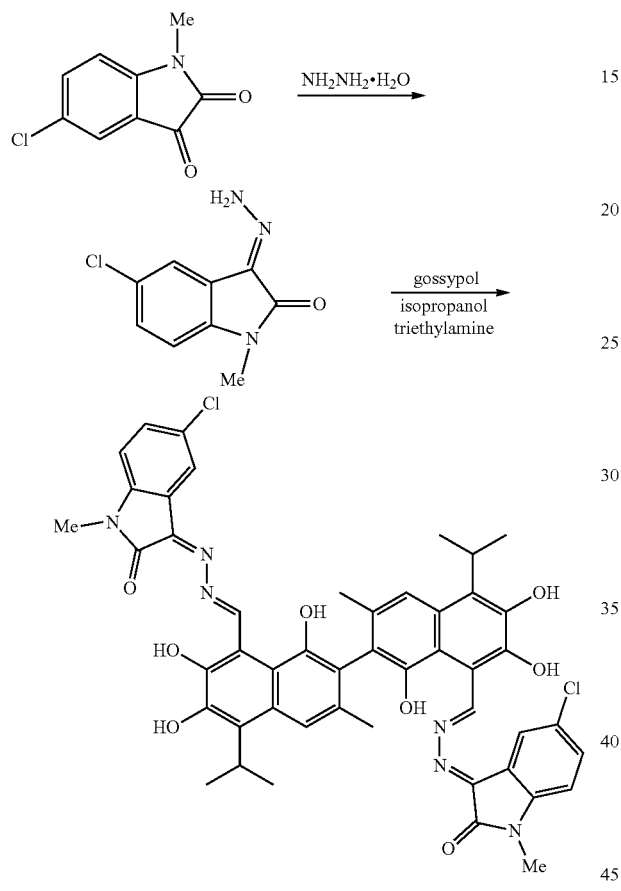

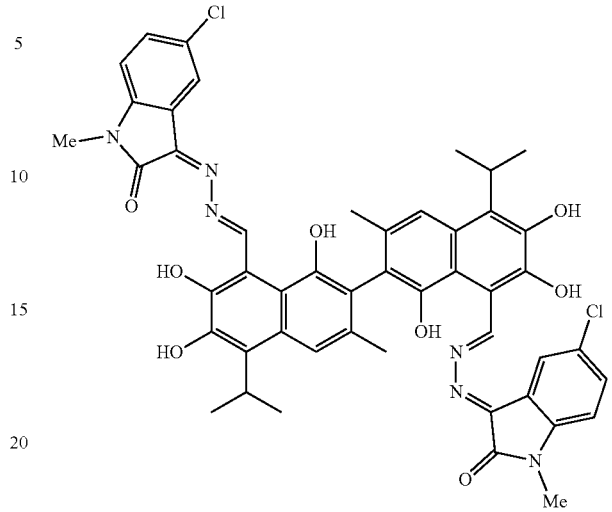

(4)

1.91 g (10 mmol) of 5-chloro-1-methylindolin-2,3-dione and 0.5 g (10 mmol) of hydrazine hydride were placed in a three-necked flask and dissolved in 100 mL isopropanol. The solution was heated and stirred at 80° C. for 6 hours. After the reaction was complete, the reaction mixture was filtered when it was hot and washed with isopropanol. The filtrate was cooled and filtered to obtain an intermediate compound. The intermediate compound and 2.59 g (5 mmol) of gossypol were placed in a reactor, and 0.7 mL triethylamine and 50 mL of isopropanol were added. The mixture was then heated and stirred at 80° C. for 10 hours. When thin layer chromatograph (TLC) indicated that the reaction is complete, the reaction mixture was concentrated under reduced pressure. The mixture was cooled to room temperature, filtered, and washed with warm water to give a crude product. The crude product was recrystallized in 25 mL isopropanol to give 0.94 g of compound (4) as a gray brown crystalline powder, a yield of 21.89%.

Gray brown crystalline powder, M.P. 204.3° C. $^1$H-NMR (400 MHz, DMSO-d$_6$) δ (ppm): 9.23 (2H, s), 8.66 (2H, s), 7.86 (2H, d), 7.34 (2H, s), 7.10 (2H, d), 6.21 (6H, s), 4.09 (6H, s), 3.26 (2H, m), 3.08 (6H, s), 2.03 (12H, d); $^{13}$C-NMR (100 MHz, DMSO-d$_6$) δ (ppm): 167.2, 155.4, 150.4, 148.1, 145.3, 139.9, 139.1, 134.7, 133.3, 131.5, 129.8, 126.4, 120.9, 119.5, 113.1, 103.0, 31.6, 29.1, 26.7; MS (ESI) for (M+H)$^+$: 901.3.

Example 5: Preparation of Compound (5), (3Z,3'E)-3,3'-(((1E, 1'E)-(1,1',6,6',7,7'-hexahydroxy-5,5'-diisopropyl-3,3'-dimethyl-[2,2'-binaphthalene]-8,8'-diyl)bis(methanylylidene))bis(hydrazine-2,1-diylidene))bis(5-chloro-1-ethylindolin-2-one)

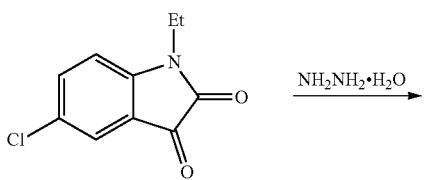

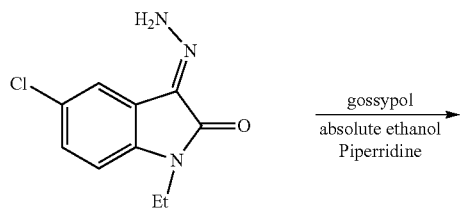

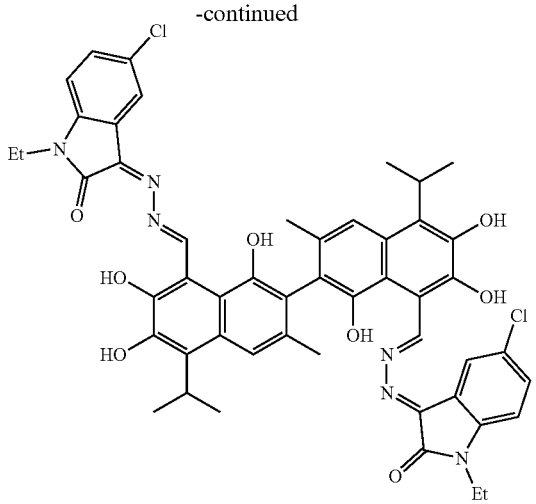

2.09 g (10 mmol) of 5-chloro-1-ethylindolin-2,3-dione and 0.75 g (15 mmol) of hydrazine hydride were placed in a three-necked flask and dissolved in 100 mL ethanol. The solution was heated and stirred at 75° C. for 10 hours. After the reaction was complete, the reaction mixture was filtered when it was hot and washed with ethanol. The filtrate was cooled and filtered to obtain an intermediate compound. The intermediate compound and 1.71 g (3.3 mmol) of gossypol were placed in a reactor, and 0.056 g piperidine and 50 mL of anhydrous ethanol were added. The mixture was then heated and stirred at 75° C. for 8 hours. When thin layer chromatograph (TLC) indicated that the reaction is complete, the reaction mixture was concentrated under reduced pressure. The mixture was cooled to room temperature, filtered, and washed with warm water to give a crude product. The crude product was recrystallized in 25 mL ethanol to give 1.42 g of compound (5) as a white powder, a yield of 38.56%.

(5)

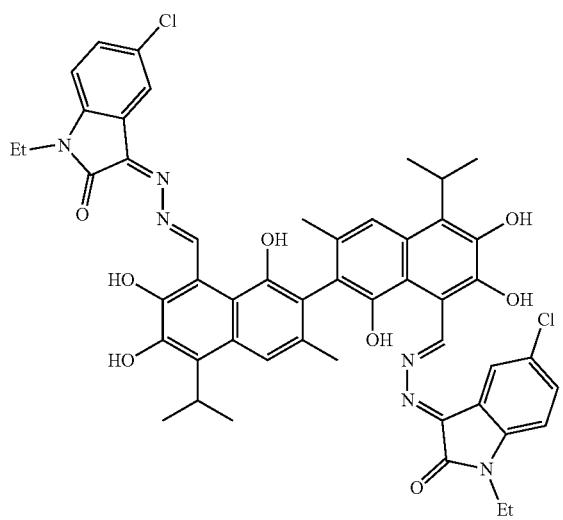

White crystalline powder, M.P. 212.5° C. $^1$H-NMR (400 MHz, DMSO-$d_6$) δ (ppm): 8.46 (1H, s), 8.37 (1H, s), 7.98 (2H, s), 7.78 (2H, d), 7.65 (2H, s), 7.50 (2H, d), 5.22 (6H, s), 4.10 (4H, m), 2.80 (2H, m), 2.68 (6H, s), 1.30-1.34 (18H, m); $^{13}$C-NMR (100 MHz, DMSO-$d_6$) δ (ppm): 163.0, 153.7, 150.4, 145.1, 143.6, 138.5, 132.0, 131.7, 130.1, 128.3, 124.0, 118.4, 117.7, 112.5, 103.4, 42.0, 27.2, 24.4, 13.3; MS (ESI) for (M+H)$^+$: 929.3.

Example 6: Preparation of Compound (6), (3Z,3'E)-3,3'-(((1E,1'E)-(1,1',6,6',7,7'-hexahydroxy-5,5'-diisopropyl-3,3'-dimethyl-[2,2'-binaphthalene]-8,8'-diyl)bis(methanylylidene))bis(hydrazine-2,1-diylidene))bis(5-chloro-1-isopropylindolin-2-one)

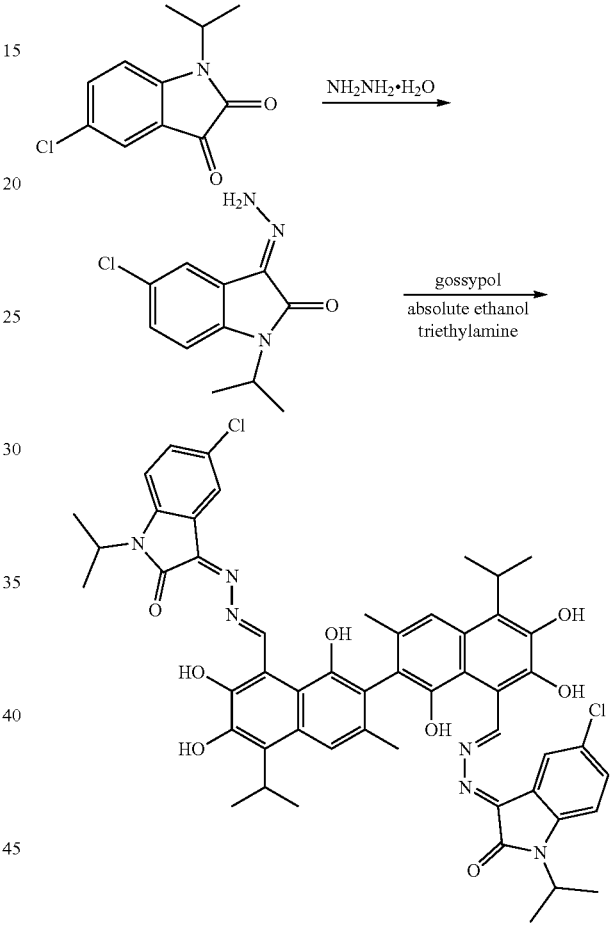

2.71 g (10 mmol) of 5-chloro-1-isopropylindolin-2,3-dione and 0.5 g (10 mmol) of hydrazine hydride were placed in a three-necked flask and dissolved in 100 mL ethanol. The solution was heated and stirred at 75° C. for 4 hours. After the reaction was complete, the reaction mixture was filtered when it was hot and washed with ethanol. The filtrate was cooled and filtered to obtain an intermediate compound. The intermediate compound and 2.07 g (4 mmol) of gossypol were placed in a reactor, and 0.48 mL triethylamine and 50 mL of anhydrous ethanol were added. The mixture was then heated and stirred at 75° C. for 10 hours. When thin layer chromatograph (TLC) indicated that the reaction is complete, the reaction mixture was concentrated under reduced pressure. The mixture was cooled to room temperature, filtered, and washed with warm water to give a crude product. The crude product was recrystallized in 25 mL ethanol to give 1.28 g of compound (6) as a gray crystalline powder, a yield of 33.56%.

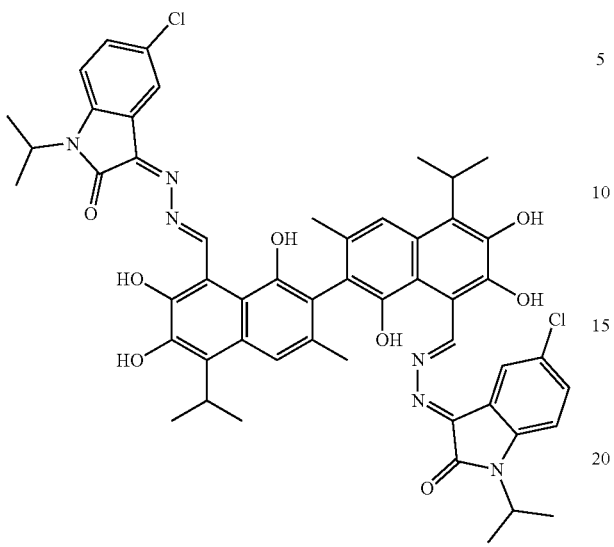
(6)
Gray crystalline powder, M.P. 216.3° C. $^1$H-NMR (400 MHz, DMSO-$d_6$) δ (ppm): 8.43 (2H, s), 7.98 (2H, s), 7.72 (2H, d), 7.65 (2H, s), 7.50 (2H, d), 5.22 (6H, s), 4.01 (2H, m), 2.90 (2H, m), 2.68 (6H, s), 1.29 (12H, d), 1.18 (12H, d); $^{13}$C-NMR (100 MHz, DMSO-$d_6$) δ (ppm): 163.0, 153.7, 150.4, 145.9, 144.6, 138.5, 132.0, 131.7, 130.1, 128.3, 124.0, 118.7, 117.2, 112.5, 101.7, 58.9, 27.2, 24.4, 20.3; MS (ESI) for (M+H)$^+$: 957.3.
Example 7: Preparation of Compound (7), (3Z,3'E)-3,3'-(((1E, 1'E)-(1,1',6,6',7,7'-hexahydroxy-5,5'-diisopropyl-3,3'-dimethyl-[2,2'-binaphthalene]-8,8'-diyl)bis(methanylylidene))bis(hydrazine-2,1-diylidene))bis(1-benzyl-5-chloroindolin-2-one)
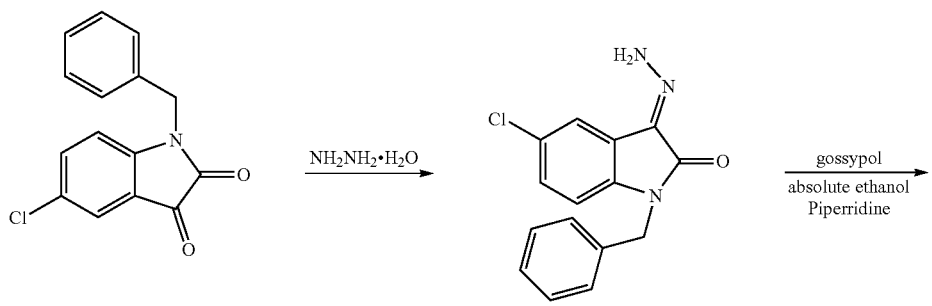
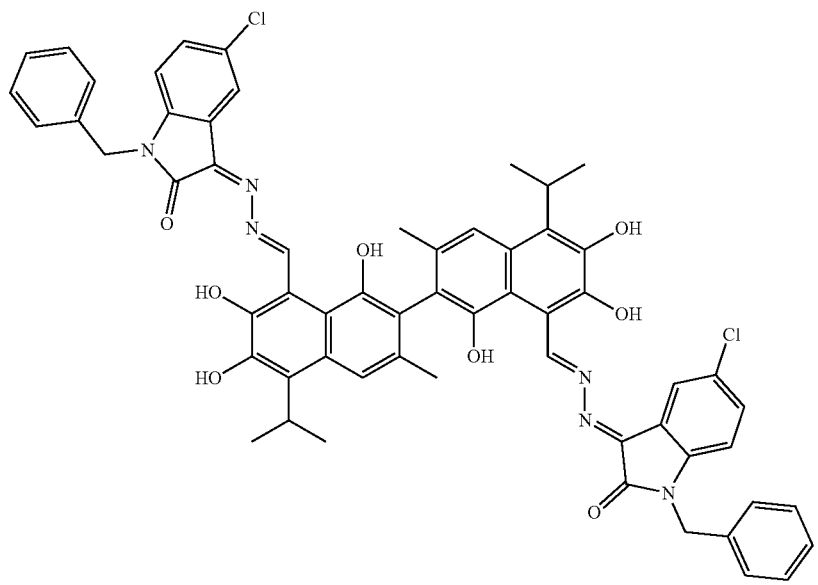

2.71 g (10 mmol) of 1-benzyl-5-chloroindolin-2,3-dione and 0.75 g (15 mmol) of hydrazine hydride were placed in a three-necked flask and dissolved in 100 mL ethanol. The solution was heated and stirred at 75° C. for 6 hours. After the reaction was complete, the reaction mixture was filtered when it was hot and washed with ethanol. The filtrate was cooled and filtered to obtain an intermediate compound. The intermediate compound and 2.59 g (5 mmol) of gossypol were placed in a reactor, and 0.85 g piperridine and 50 mL of anhydrous ethanol were added. The mixture was then heated and stirred at 75° C. for 14 hours. When thin layer chromatograph (TLC) indicated that the reaction is complete, the reaction mixture was concentrated under reduced pressure. The mixture was cooled to room temperature, filtered, and washed with warm water to give a crude product. The crude product was recrystallized in 25 mL ethanol to give 2.17 g of compound (7) as a dark yellow crystalline powder, a yield of 41.30%.

(7)

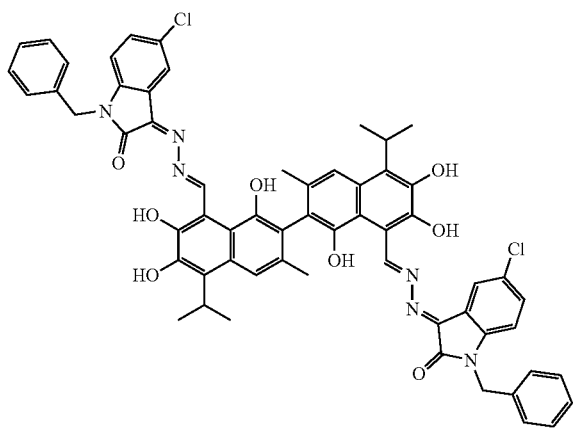

Dark yellow crystalline powder, M.P. 223.8° C. $^1$H-NMR (400 MHz, DMSO-$d_6$) δ (ppm): 8.46 (1H, s), 8.37 (1H, s), 7.98 (2H, s), 7.72 (2H, d), 7.65 (2H, s), 7.50 (2H, d), 7.23-7.36 (10H, m), 5.22 (6H, s), 5.00 (4H, s), 2.90 (2H, m), 2.68 (6H, s), 1.29 (12H, d); $^{13}$C-NMR (100 MHz, DMSO-$d_6$) δ (ppm): 163.0, 153.7, 150.4, 145.9, 144.6, 138.5, 136.0, 132.7, 131.1, 129.8, 128.0, 126.7, 124.2, 119.5, 117.7, 112.9, 101.2, 47.4, 27.3, 24.2; MS (ESI) for (M+H)$^+$: 1053.3.

Example 8: Preparation of Compound (8), (3Z,3'E)-3,3'-(((1E, 1'E)-(1,1',6,6',7,7'-hexahydroxy-5,5'-di-isopropyl-3,3'-dimethyl-[2,2'-binaphthalene]-8,8'-diyl)bis(methanylylidene))bis(hydrazine-2,1-diylidene))bis(1-benzylindolin-2-one)

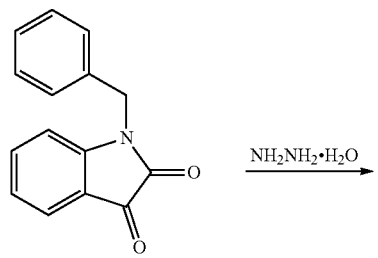

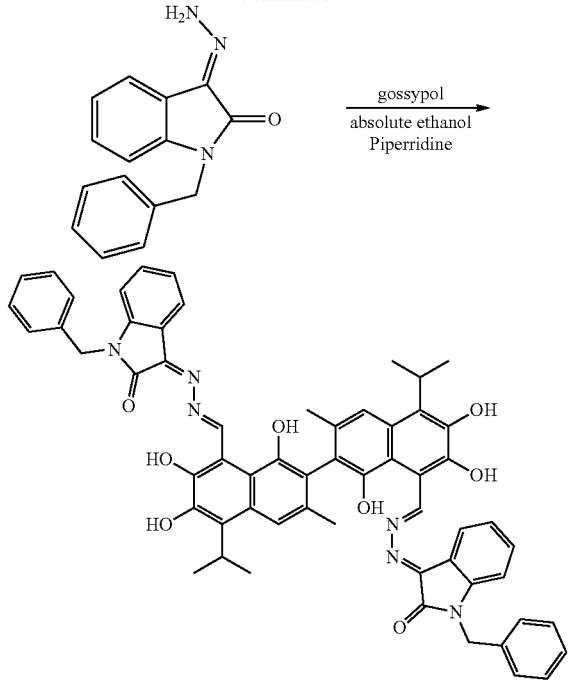

2.37 g (10 mmol) of 1-benzylindolin-2,3-dione and 0.75 g (15 mmol) of hydrazine hydride were placed in a three-necked flask and dissolved in 100 mL ethanol. The solution was heated and stirred at 60° C. for 6 hours. After the reaction was complete, the reaction mixture was filtered when it was hot and washed with ethanol. The filtrate was cooled and filtered to obtain an intermediate compound. The intermediate compound and 2.07 g (4 mmol) of gossypol were placed in a reactor, and 0.68 g piperridine and 50 mL of anhydrous ethanol were added. The mixture was then heated and stirred at 75° C. for 10 hours. When thin layer chromatograph (TLC) indicated that the reaction is complete, the reaction mixture was concentrated under reduced pressure. The mixture was cooled to room temperature, filtered, and washed with warm water to give a crude product. The crude product was recrystallized in 25 mL ethanol to give 1.46 g of compound (8) as a dark brown crystalline powder, a yield of 37.19%.

(8)

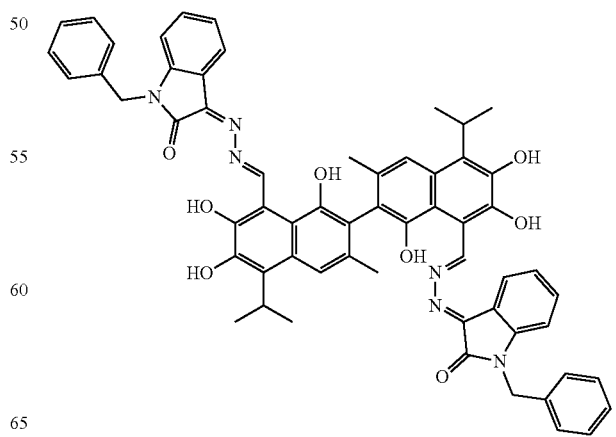

Dark brown crystalline powder, M.P. 219.9° C. $^1$H-NMR (400 MHz, DMSO-d$_6$) δ (ppm): 8.46 (1H, s), 8.37 (1H, s), 7.87-7.79 (4H, m), 7.65 (2H, s), 7.53 (2H, t), 7.36-7.23 (12H, m), 5.22 (6H, s), 5.00 (4H, s), 2.90 (2H, m), 2.68 (6H, s), 1.29 (12H, d); $^{13}$C-NMR (100 MHz, DMSO-d$_6$) δ (ppm): 163.0, 153.7, 150.4, 147.9, 146.0, 144.6, 138.5, 136.0, 132.7, 131.1, 129.8, 128.0, 126.7, 124.2, 119.5, 117.7, 115.9, 111.2, 101.0, 47.1, 27.2, 24.2; MS (ESI) for (M+H)$^+$: 985.4.

Example 9

The Anti-Tumor Activity Test of the Compounds of the Present Invention

The compounds of the present invention were subjected to tumor cell proliferation inhibition test, and conventional MTT method was used.

Cell lines: human hepatoma cells (HepG2), human lung cancer cells (A-549), human gastric cancer cells (SGC-7901). The culture medium was DMEM+15% NBS+double antibody.

Sample solution preparation: after dissolving with DMSO (Merck), PBS (−) was added to obtain 100 μmol/L solution or homogeneous suspension. The solution was diluted with PBS (−) in DMSO to a final concentration of 0.1, 1, 10, 20, 40, 60, 80, 100 μmol/L.

Gossypol was used as control solution, prepared under the same condition.

Cell culture: adherent growth Tumor cells were cultured in 1640 medium containing 10% inactivated neonatal bovine serum and penicillin, streptomycin (1 million U/L), placed in carbon dioxide incubator at 37° C., 5% CO$_2$, and saturated humidity. Cells were treated serially passaged 2-3 times. The first culture was washed with PBS 2 times, and digested with trypsin. Fresh culture medium was added evenly, cells were adjusted to a appropriate concentration and transferred into a new culture flask. Cell in an exponential phase were chosen for the tests.

MTT Assay for Cell Viability and IC$_{50}$ Determination

Experimental Principle: Living cells mitochondria in the dehydrogenase can reduce yellow MTT to water-insoluble blue-violet product MT (MTT formazan), deposited in the cells. The amount of production is proportional to the number of living cells. Dead cells do not reduce yellow MTT. DMSO can dissolve blue violet crystals, and the color depth is proportional to the amount contained, so the absorbance measured by the microplate reader can reflect the cell viability.

Methods: The exponential phase cells were digested and counted and seeded in 96-well plates at a density of 2×104/mL at 100 μl per well. After 24 hours of incubation, the cells to be tested were treated with 0.1, 1, 10, 20, 40, 60, 80, 100 μmol/L of the compounds. Each experimental group had 5 wells in each concentration, and the culture medium containing 0.4% DMSO was used as control. After 48 hours, the supernatant was discarded, and 100 μl of MTT ((2-(4,5-dimethyl-2-thiazolyl)-3,5-diphenyl-2H-tetrazole hydrobromide) (1 mg/mL) was added to each well. After another 4 hours, the supernatant was discarded, and 100 μl of DMSO was added to each well. After mixing, the absorbance was measured at 570 nm using a microplate reader. An IC$_{50}$ calculation software was used to determine the half inhibitory concentration (IC$_{50}$).

The test results are shown in Table 1. The compounds listed in the table correspond to the compounds described above.

TABLE 1

Half Inhibitory Concentration of Compounds on Different Tumor Cells IC$_{50}$ (unit: μmol/L)

| Compounds | IC$_{50}$(μmol/L) | | |
|---|---|---|---|
| | HepG2 | A549 | SGC-7901 |
| 1 | >100 | >100 | >100 |
| 2 | 29.45 ± 2.10 | 68.33 ± 2.15 | >100 |
| 3 | 8.67 ± 0.74 | 7.87 ± 0.91 | 16.57 ± 1.46 |
| 4 | >100 | >100 | >100 |
| 5 | 8.92 ± 0.59 | 19.32 ± 1.62 | 13.72 ± 1.11 |
| 6 | >100 | 66.45 ± 2.53 | >100 |
| 7 | 14.71 ± 1.12 | 16.33 ± 1.21 | 12.45 ± 1.93 |
| 8 | >100 | >100 | 88.76 ± 3.02 |
| Gossypol | 9.55 ± 0.41 | 12.96 ± 0.32 | 19.81 ± 0.66 |

The results show that compound (3) has excellent antitumor activities in the three cell lines tested. Compounds (5) and (7) also show good activities. The above experimental results indicate that the compounds of the present invention have good antitumor activities. Some compounds even have equal or better activities than Gossypol against certain cell lines. These compounds can be used for the study of antitumor research and drug development.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:
1. A compound of formula I:

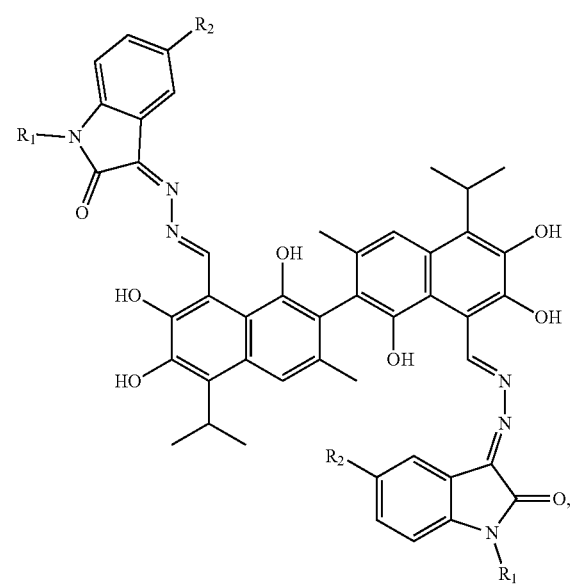

wherein R$_1$ and R$_2$ are independently hydrogen, alkyl, cycloalkyl, alkoxy, nitro, halogen, unsubstituted or substituted phenyl, or unsubstituted or substituted benzyl.
2. The compound of claim 1, wherein R₁ is independently hydrogen, alkyl, or benzyl.
3. The compound of claim 1, wherein R₂ is independently hydrogen, alkyl, or halogen.
4. The compound of claim 1, wherein the compound is selected from the group consisting of:
(1)
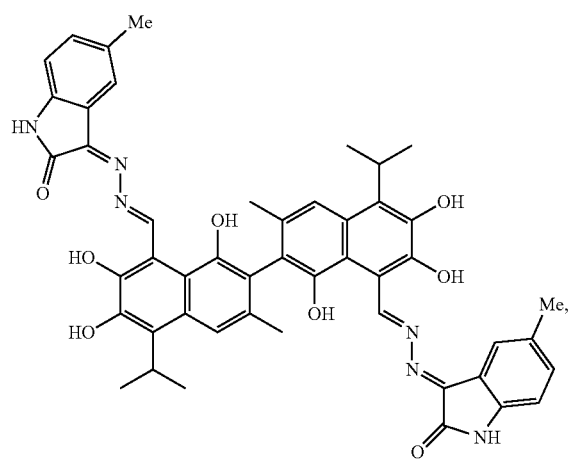
(2)
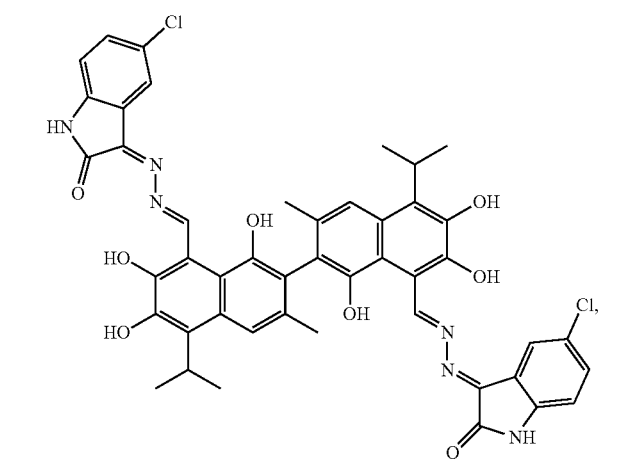
(3)
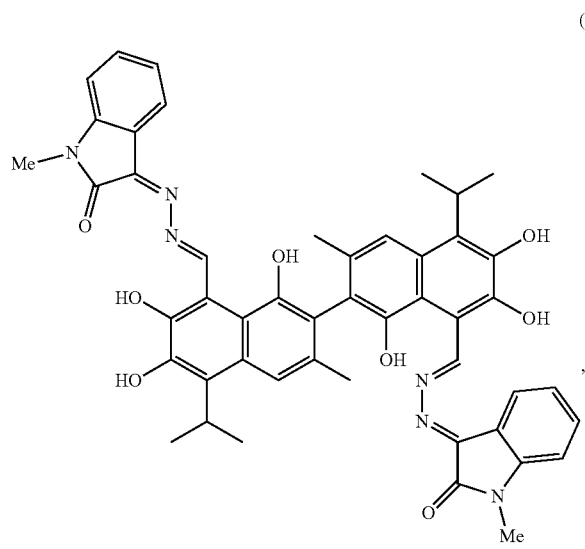
(4)
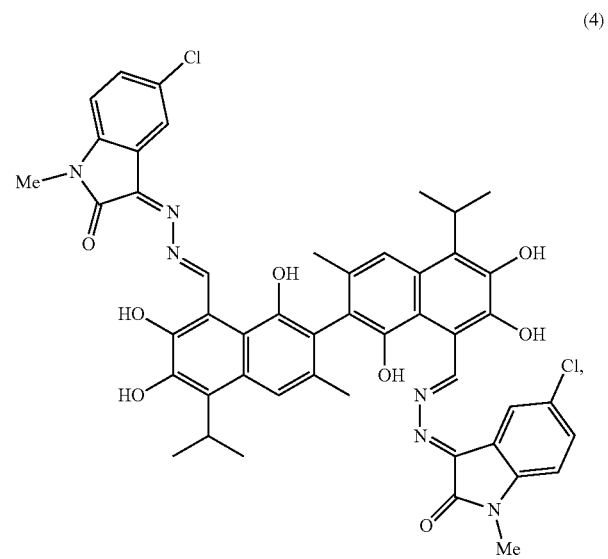

(5)
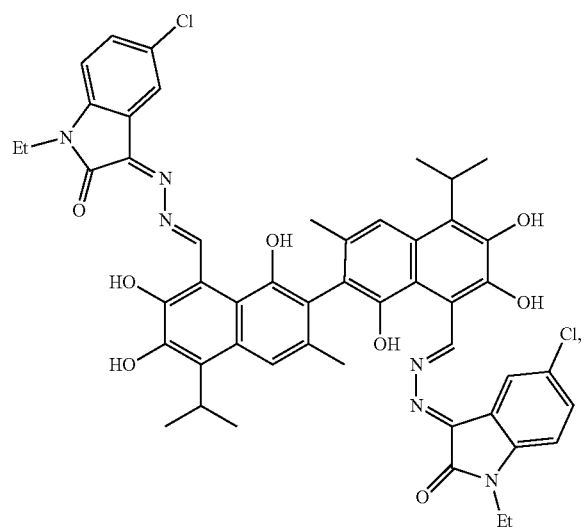
(6)
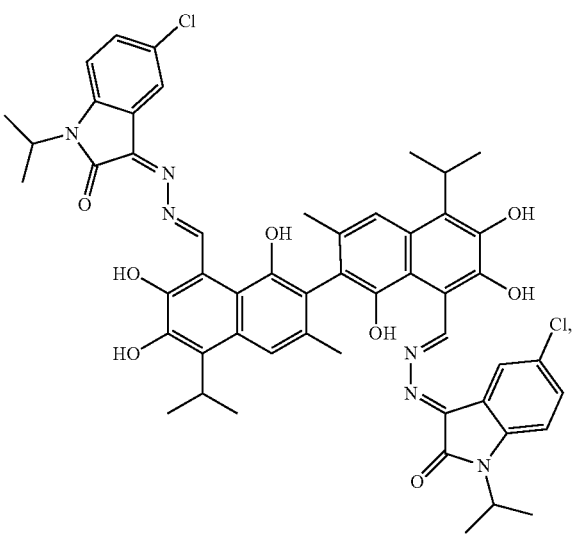
(7)
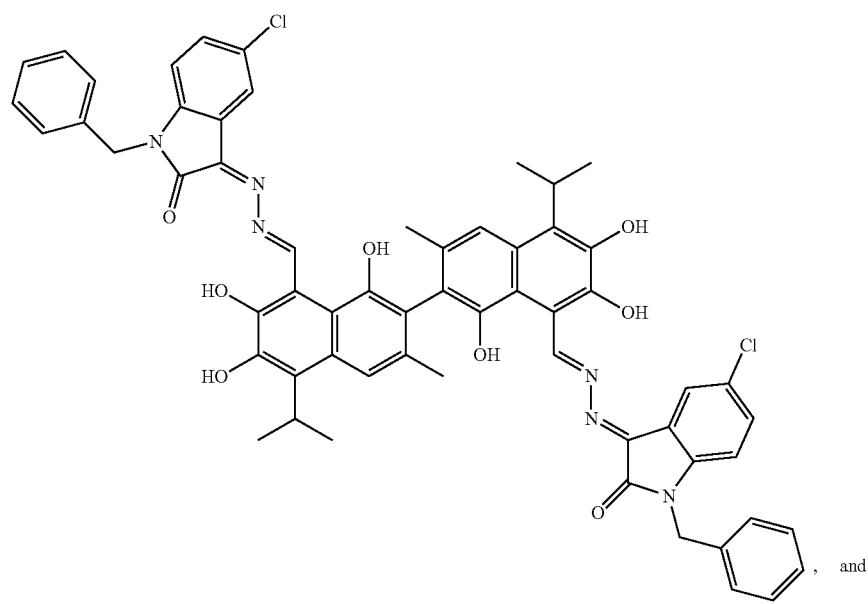
, and

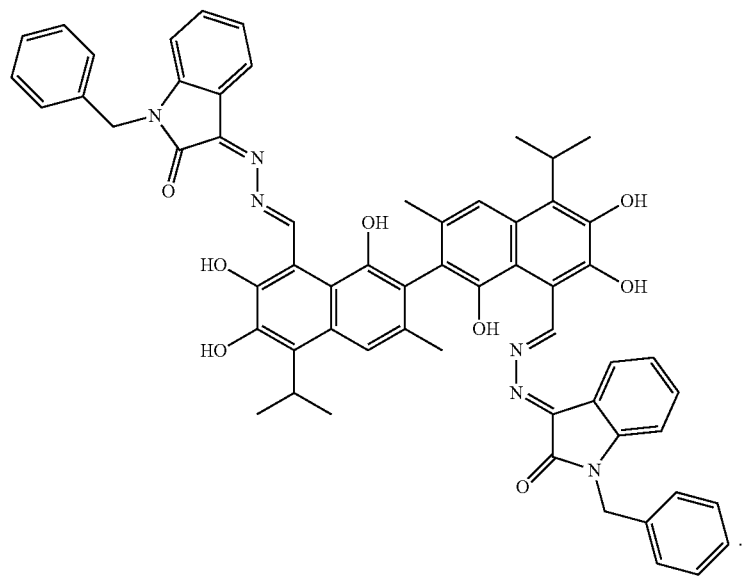

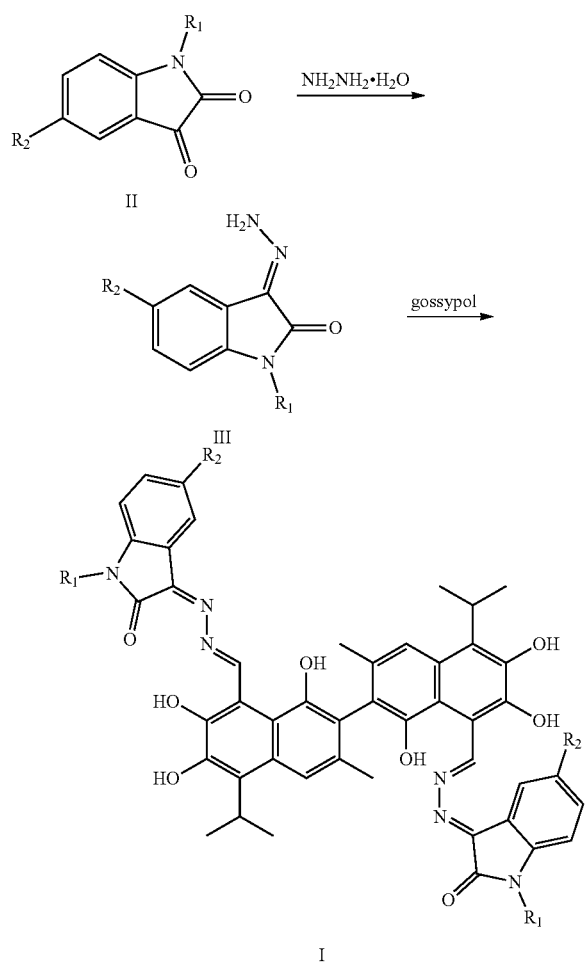

5. A method of preparing the compound of claim 1, comprising:

(1) reacting a compound of formula II and hydrazine hydrate ($N_2H_4 \cdot H_2O$) in an organic solvent to obtain a compound of formula III; and (2) reacting the compound of formula III with gossypol in the presence of a catalyst in the organic solvent to obtain the compound of formula I, wherein $R_1$ and $R_2$ are independently hydrogen, alkyl, cycloalkyl, alkoxy, nitro, halogen, unsubstituted or substituted phenyl, or unsubstituted or substituted benzyl.

6. The method of claim 5, wherein the organic solvent is methanol, ethanol, or isopropanol.

7. The method of claim 6, wherein the organic solvent is ethanol.

8. The method of claim 5, wherein the compound of formula II and hydrazine hydrate ($N_2H_4 \cdot H_2O$) are heated in the organic solvent to 60-100° C. for 4 to 10 hours.

9. The method of claim 5, wherein the compound of formula III and gossypol are heated in the organic solvent to 60-100° C. for 8 to 14 hours.

10. The method of claim 5, further comprising:
recrystallizing the compound of formula I in the organic solvent.

11. The method of claim 5, wherein a molar ratio of the compound of formula II to hydrazine hydrate ($N_2H_4 \cdot H_2O$) is 1:1 to 1:2.5.

12. The method of claim 9, wherein the molar ratio of the compound of formula II to hydrazine hydrate ($N_2H_4H_2O$) is 1:1.5.

13. The method of claim 5, wherein a molar ratio of the compound of formula III to gossypol is 2:1 to 3:1.

14. The method of claim 13, wherein the molar ratio of the compound of formula III to gossypol is 2.5:1.

15. The method of claim 5, wherein the catalyst is piperidine or triethylamine.

* * * * *